US 8,730,048 B2
(12) United States Patent
Shen et al.

(10) Patent No.: US 8,730,048 B2
(45) Date of Patent: May 20, 2014

(54) EARPHONE-BASED GAME CONTROLLER AND HEALTH MONITOR

(75) Inventors: Guo Bin Shen, Beijing (CN); Xiaofan Jiang, Beijing (CH)

(73) Assignee: Microsoft Corporation, Redmond, WA (US)

( * ) Notice: Subject to any disclaimer, the term of this patent is extended or adjusted under 35 U.S.C. 154(b) by 141 days.

(21) Appl. No.: 13/526,331

(22) Filed: Jun. 18, 2012

(65) Prior Publication Data

US 2013/0335226 A1 Dec. 19, 2013

(51) Int. Cl.
 G08B 23/00 (2006.01)
 H04S 7/00 (2006.01)
 H04R 5/033 (2006.01)

(52) U.S. Cl.
 CPC ............... *H04S 7/304* (2013.01); *H04R 5/033* (2013.01)
 USPC .......................................... 340/573.1; 381/74

(58) Field of Classification Search
 CPC .......... H04S 7/304; H04S 7/303; H04S 5/033
 USPC .................. 340/573.1, 692; 381/74, 309, 310
 See application file for complete search history.

(56) References Cited

U.S. PATENT DOCUMENTS

| | | | | |
|---|---|---|---|---|
| 5,844,816 A * | 12/1998 | Inanaga et al. | | 381/74 |
| 7,756,274 B2 * | 7/2010 | Layton et al. | | 381/17 |
| 7,769,435 B2 | 8/2010 | Kuo et al. | | |
| 2007/0297618 A1 | 12/2007 | Nurmi et al. | | |
| 2008/0076972 A1 | 3/2008 | Dorogusker et al. | | |
| 2008/0211768 A1 | 9/2008 | Breen et al. | | |
| 2009/0296951 A1 * | 12/2009 | De Haan | | 381/74 |
| 2010/0113150 A1 | 5/2010 | Chan et al. | | |
| 2010/0217098 A1 | 8/2010 | LeBoeuf et al. | | |
| 2012/0002822 A1 * | 1/2012 | Peissig et al. | | 381/74 |
| 2012/0114132 A1 * | 5/2012 | Abrahamsson et al. | | 381/74 |
| 2013/0057571 A1 * | 3/2013 | Harris | | 345/619 |
| 2013/0233078 A1 * | 9/2013 | Sinclair | | 73/514.32 |
| 2013/0279724 A1 * | 10/2013 | Stafford et al. | | 381/309 |

OTHER PUBLICATIONS

Healy, et al. "Spatially Augmented Audio Delivery: Applications of Spatial Sound Awareness in Sensor-Equipped Indoor Environments" 2009 Tenth International Conference on Mobile Data Management: Systems, Services and Middleware; 5 pages.

(Continued)

*Primary Examiner* — John A Tweel, Jr.
(74) *Attorney, Agent, or Firm* — Carole Boelitz; Micky Minhas; Lee & Hayes

(57) ABSTRACT

Design and operation techniques for an earphone-based game controller and health monitor are described herein. In one example, two "ear bud" style earphones are configured as I/O devices, each including a speaker to output sound and an accelerometer to receive an input of motion imparted by a user. The I/O devices may be connected to a mobile device, such as a cellular phone. Accordingly, the I/O devices may be inserted into a user's ears for listening or may be used as game controllers, such as by moving one I/O device in each hand. In a further example, a thermometer may be used in at least one of the I/O devices, and may gather health data by measuring the temperature of the user. And in a further example, a microphone may be used in at least one I/O device to gather heart rate and respiration-quality data regarding the user.

20 Claims, 8 Drawing Sheets

(56) References Cited

OTHER PUBLICATIONS

Motorola SF500: Puts Heart Into Your Workout http://www.motorola.com/Consumers/US-EN/Consumer-Product-and-Services/Mobile+Phone+Accessories/MOTOACTV-Accessories/MOTOROLA-SF500-US-EN#anchor retrieved Dec. 22, 2011, 2 pages.

Poh, et al. "Heartphones: Sensor Earphones and Mobile Application for Non-obtrusive Health Monitoring" 2009 International Symposium on Wearable Computers; 2 pages.

Project HiJack, http://www.eecs.umich.edu/~prabal/projects/hijack/ retrieved Dec. 22, 2011, 3 pages.

\* cited by examiner

EARPHONE-BASED GAME CONTROLLER AND HEALTH MONITOR

BACKGROUND

Cellular telephones and music-playback devices frequently are sold as a package, including the hand unit (the phone), a charger and earphones. Because earphones are so routinely supplied by manufacturers, they are increasingly used with small mobile devices such as cellular telephones and music players. While "over-the-ear" phones are known, smaller "ear bud" earphones are more commonly used. Such stereo earphones may include a 3.5 mm plug (or similar) for attachment to the cell phone.

However, while earphones are quite common, they are also somewhat limited in functionally. As a result, only limited use is made of the earphone jack into which they are connected.

SUMMARY

Techniques for the design and operation of an earphone-based game controller and health monitor are described herein. In one example, two "ear bud" style earphones are configured as I/O devices, each including a speaker to output sound and an accelerometer to receive input in the form of motion imparted by a user. The I/O devices may be connected to a mobile device, such as a cellular phone. Software applications running on the mobile device may provide an output signal to the I/O devices and receive input data from them. In one example, the I/O devices may be used as output devices that provide sound that may be heard when the I/O devices are inserted into a user's ears. Alternatively, the I/O devices may be used as input devices, such as game controllers, by moving one accelerometer-equipped I/O device in each hand. In a further example, a thermometer may be used in at least one of the I/O devices, and may gather health data by measuring a body temperature of the user. And in a still further example, a microphone may be used in at least one I/O device to gather heart rate and respiration-quality data.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The term "techniques," for instance, may refer to device(s), system(s), method(s) and/or computer-readable instructions as permitted by the context above and throughout the document.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components. Moreover, the figures are intended to illustrate general concepts, and not to indicate required and/or necessary elements.

DETAILED DESCRIPTION

Overview

The disclosure describes examples of the design and operation of an earphone-based game controller and health monitor. In one example, accelerometers in each of two "ear bud" style earphones may be separately manipulated. Separate accelerometer data from the two accelerometers is provided to software, such as a video game, operating on a mobile device, such as a cell phone. Additional sensors in one or both earphones, such as a thermometer, a microphone and others, allow the ear buds to obtain health data from a user. For example, sensors in the ear buds may allow tracking of the user's body temperature, heart rate, respiration rate, respiration effectiveness (e.g., congestion, coughing, wheezing, etc.) and other factors. Additionally, the earphone-based game controller and health monitor may protect the user from other dangers, such as by reporting the user falling (especially among the elderly) or reporting the approach of a car (especially among those jogging and listening to music).

The discussion herein includes several sections. Each section is intended as an example, and not to indicate limitations to the use of the techniques discussed. More particularly, this entire description is intended to illustrate components which may be utilized in an earphone-based game controller and health monitor, but not components which are necessarily required. The discussion begins with a section entitled "Example Hardware Design," which describes example design that may be used to implement the techniques described herein. This section depicts and describes example electrical connections, power generation, a microprocessor and other components in the device. Next, a section entitled "Example Software Design" describes example designs that may be used to implement the techniques described herein. This section depicts and describes example applications, application programming interfaces (APIs) and other functional software blocks in the device. Next, a section entitled "Example Methods" illustrates and describes techniques to process and manage data from a variety of input devices. Next, a section entitled "Example Accelerometer Data Handling" illustrates and describes techniques to manage data from two accelerometers, which may provide "complex" accelerometer data that is more versatile than data from a single accelerometer. Next, a section entitled "Example Health Monitor" illustrates and describes example techniques that may be used to process sensor data and to provide health information. Finally, the discussion ends with a brief conclusion.

This brief introduction, including section titles and corresponding summaries, is provided for the reader's convenience and is not intended to describe and/or limit the scope of the claims or any section of this disclosure.

Example Hardware Design

Figure 1:
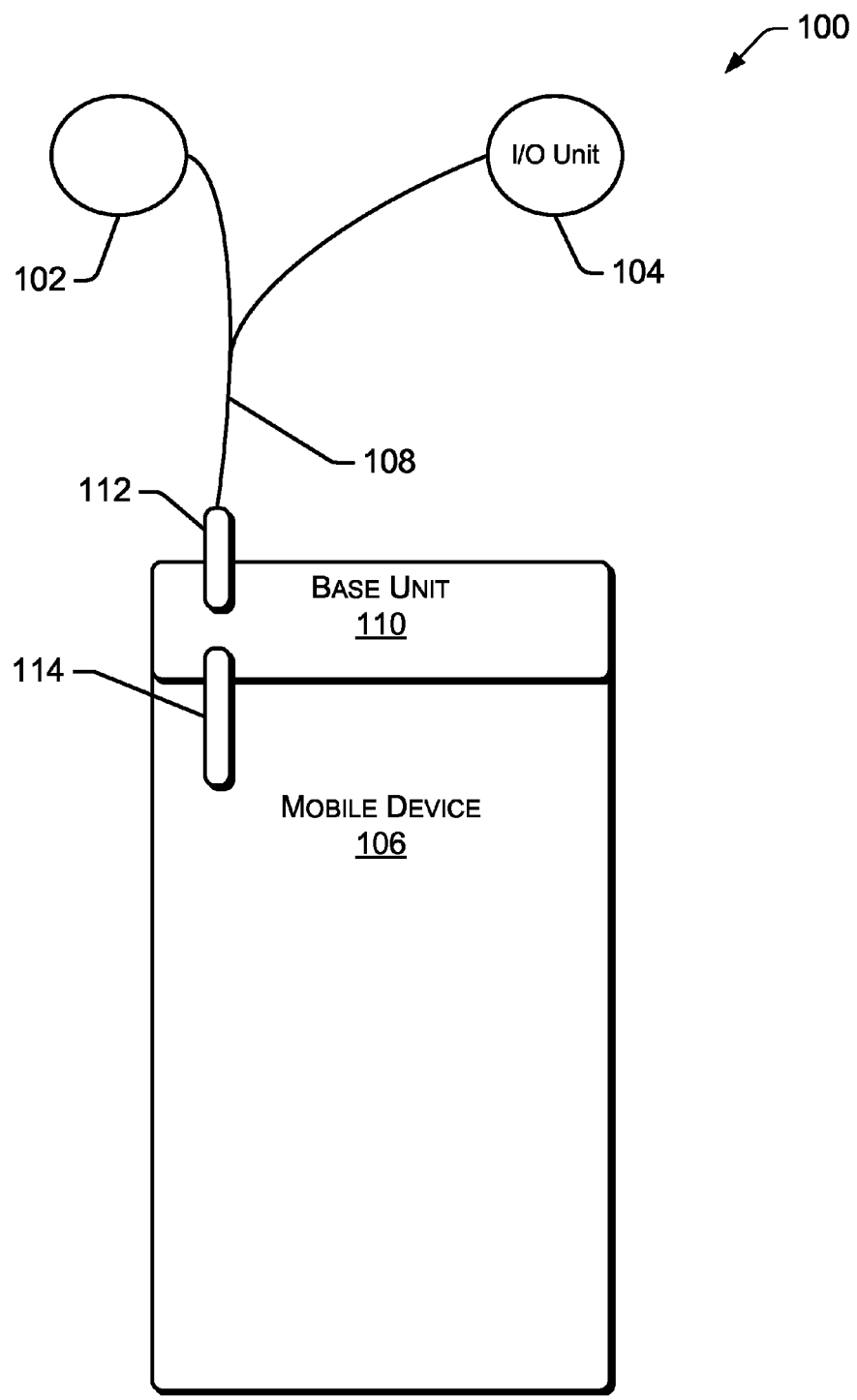
FIG. 1 is diagram showing an example earphone-based game controller and health monitor, including a pair of I/O devices, which for purposes of the example are configured to resemble "ear bud" earphones and are connected to a cellular telephone or other mobile device by a wired connection.

FIG. 1 is diagram showing an example earphone-based game controller and health monitor 100, including a pair of I/O devices 102, 104. For purposes of example, the pair of I/O devices is configured as "ear bud" earphones and is connected to a mobile device 106 such as a cellular telephone. In the example, a wired connection 108 is used; however, in an alternative design, a wireless connection, such as Bluetooth, may be used.

In the example of FIG. 1, a base unit 110 is used as an interface between the I/O devices 102, 104 and the mobile device 106. Alternatively, the functionality of the base unit 110 could be provided by the I/O devices and/or the mobile device 106. The base unit 110 may be configured to provide a power supply to the I/O devices, audio signal pass-through to the I/O devices and data processing functionality. In the example of FIG. 1, an audio jack 112 (e.g., a 2.5 or 3.5 mm jack) may be used to connect the wired connection 108 of the I/O devices 102, 104 to the base unit 110. Alternatively, the wiring 108 may be connected to the base 110 directly, without the use of a removable jack. The base unit 110 may be connected to the mobile device 106 by a jack 114 (e.g., a 2.5 or 3.5 mm audio jack).

The I/O devices 102, 104 may be configured for use in the left and right ears of a user, and may each contain an output device such as a speaker. Additionally, the I/O devices 102, 104 may function as input devices; for example, one or more of the I/O devices may be configured with one or more sensors, such as accelerometer(s), thermometer(s), microphone(s), etc. In one example, an accelerometer in each I/O device 102, 104 allows the user to manipulate one I/O device in each hand to create a "complex" accelerometer input having two input motions. The input motions may be considered individually or in a combined manner by an application, such as a video game, operating on the mobile device. A thermometer in one or both I/O devices may provide data on the user's body temperature, while a microphone in one or both I/O devices may provide data on the user's heart rate, respiration rate, and/or respiration quality (coughing, wheezing, etc.) and the like. As discussed infra, these and other sensors may provide additional health benefits.

Figure 2:
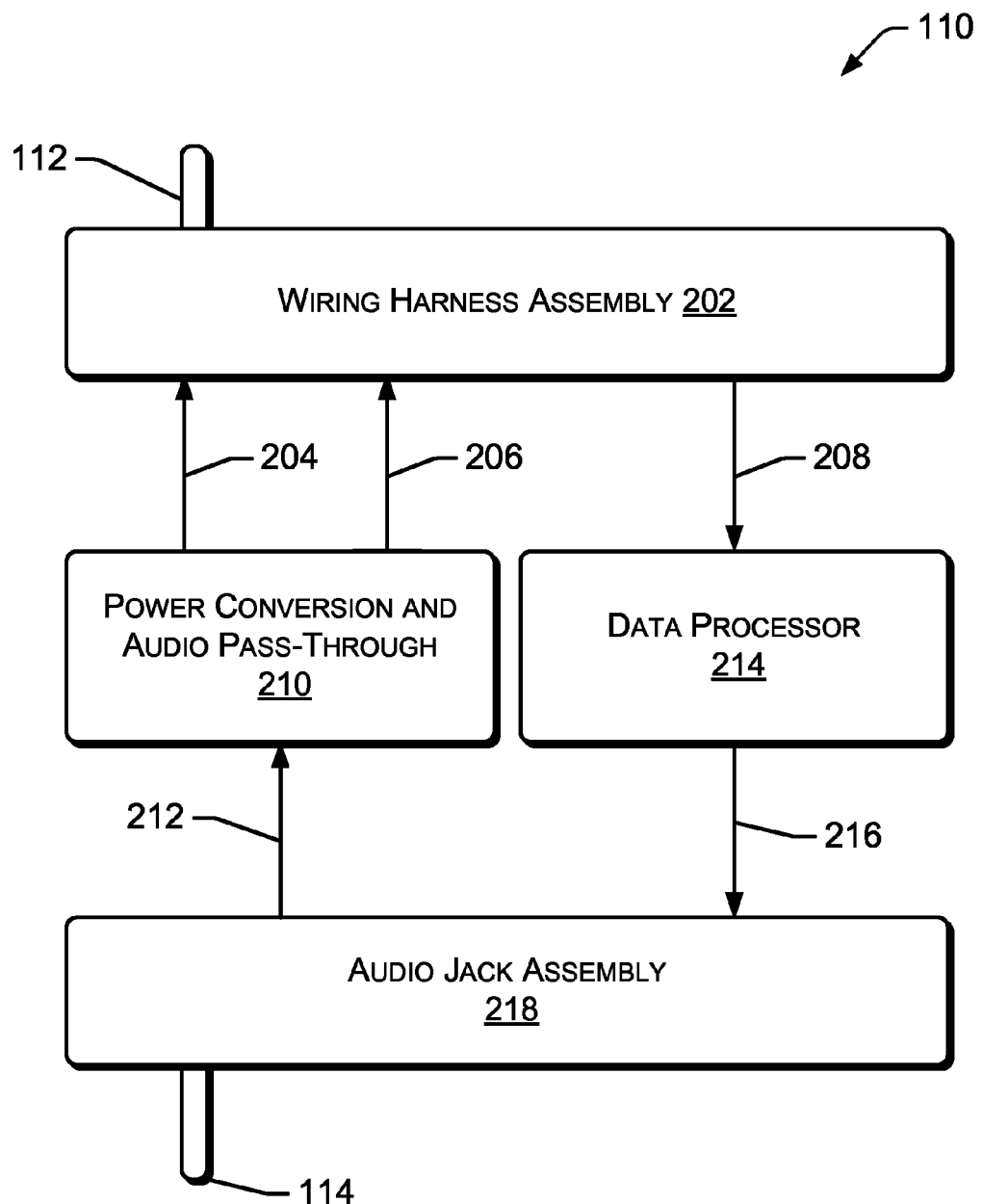
FIG. 2 is a diagram showing an example arrangement of components in a base unit of an earphone-based game controller and health monitor.

FIG. 2 is a diagram showing an example arrangement of components in a base unit 110 of an earphone-based game controller and health monitor. In the examples of FIGS. 1 and 2, the base unit 110 may provide a power supply to the I/O devices 102, 104 (see FIG. 1). Additionally, the base unit may provide audio pass-through to the speakers of the I/O devices 102, 104. That is, the base 110 may pass an audio signal from the mobile device through to the I/O devices. And further, the base unit 110 may provide data processing functionality to data provided by sensor units (e.g., an accelerometer, thermometer and/or a microphone, etc.) in one or both of the I/O devices. In an alternative example, some or all of the functionality and/or components of the base unit 110 may be incorporated into the I/O devices and/or the mobile device, thereby obviating need for a base unit.

A wiring harness assembly 202 may provide electrical connectivity between components in the base 110 and one or both I/O devices. If quick connect and disconnect are desired, a jack 112 and associated socket may be provided. In one example, the jack 112 may be a terminal portion of the wiring 108 (see FIG. 1) and the socket (e.g., an earphone port) may be part of the base 110. Accordingly, the jack of the wiring 108 may be "plugged into" the socket of the base 110. Alternatively, the wiring harness 202 may be directly wired to I/O devices, thereby obviating need for the jack 112 and associated socket. In such an example, the base 110 and I/O devices 102, 104 would be wired together as a unit. In the example of FIG. 2, wiring harness may provide wiring conductors for a power line 204, an audio signal 206, and a microphone input 208. The microphone input 208 may provide data input from the I/O device(s), which may include multiplexed data from a plurality of sensors (e.g., accelerometers, a thermometer, microphone, etc.).

A power conversion and audio pass-through device 210 may receive left and right stereo inputs 212 corresponding to left and right tracks of an audio channel. As output, the power conversion and audio pass-through device 210 provides a power output conductor 204 and a pass-through audio signal 206. The power conversion and audio pass-through device 210 may be a discrete device or a functional block that may be integrated within other functional units.

The power conversion and audio pass-through device 210 may be used to provide power to devices and/or components in the base unit 110 and the I/O devices 102, 104 (see FIG. 1). Power conversion portions of the device 210 may utilize a signal on one of two stereo inputs (e.g., the left or the right track of a stereo input) as a source of power. For example, a steady tone on the left track (e.g., a steady frequency and amplitude) may be converted into a power source 204 having a desired voltage potential. By varying the signal (e.g., amplitude and frequency) the power conversion functionality may be varied to produce a desired power level.

The audio pass-through portions of the device 210 may "pass through" the audio channel not used for power generation. That is, the audio signal may pass through the device 210 with little or no alteration. In particular, the audio channel 206 may be passed through to the I/O devices 102, 104 (see FIG. 1). In one example, a "mono" signal is passed through the device 210 to both I/O devices 102, 104. Thus, one of the left or right audio channels may be used to generate power, while the other sound channel is passed through to speakers in one or both I/O devices.

A data processor 214 may be configured to process data obtained from one or more sensors within one or more of the I/O devices. The processing may include organizing the data into a format expected by one or more applications operating on the mobile device 106, multiplexing the data obtained from two I/O devices, and other tasks. The data from the plurality of sensors may include data from one or more of accelerometers, thermometers, microphones, gyroscopes, cameras, light sensitive diodes or other sensing devices provided by the I/O devices and/or the base unit 110. Output from the data processor 214 may be provided on a further segment of the microphone input 216. The data processor 214 may include a microprocessor or an application specific integrated circuit (ASIC), and may include a memory device, an I/O device or gate(s) and/or any logic circuitry indicated by a particular application or use.

An audio jack assembly 218 may electrically connect the left and right stereo audio conductors 212 and the segment of the microphone input 216 with the jack 114. Thus, the audio jack assembly 218 may include wiring connections required to establish electrical connection to the mobile device 106. The connections may include the jack 114, configured to plug into the mobile device 106 and connections to the power conversion and audio pass-through device 210 and the data processor 214 to the mobile device.

Figure 3:
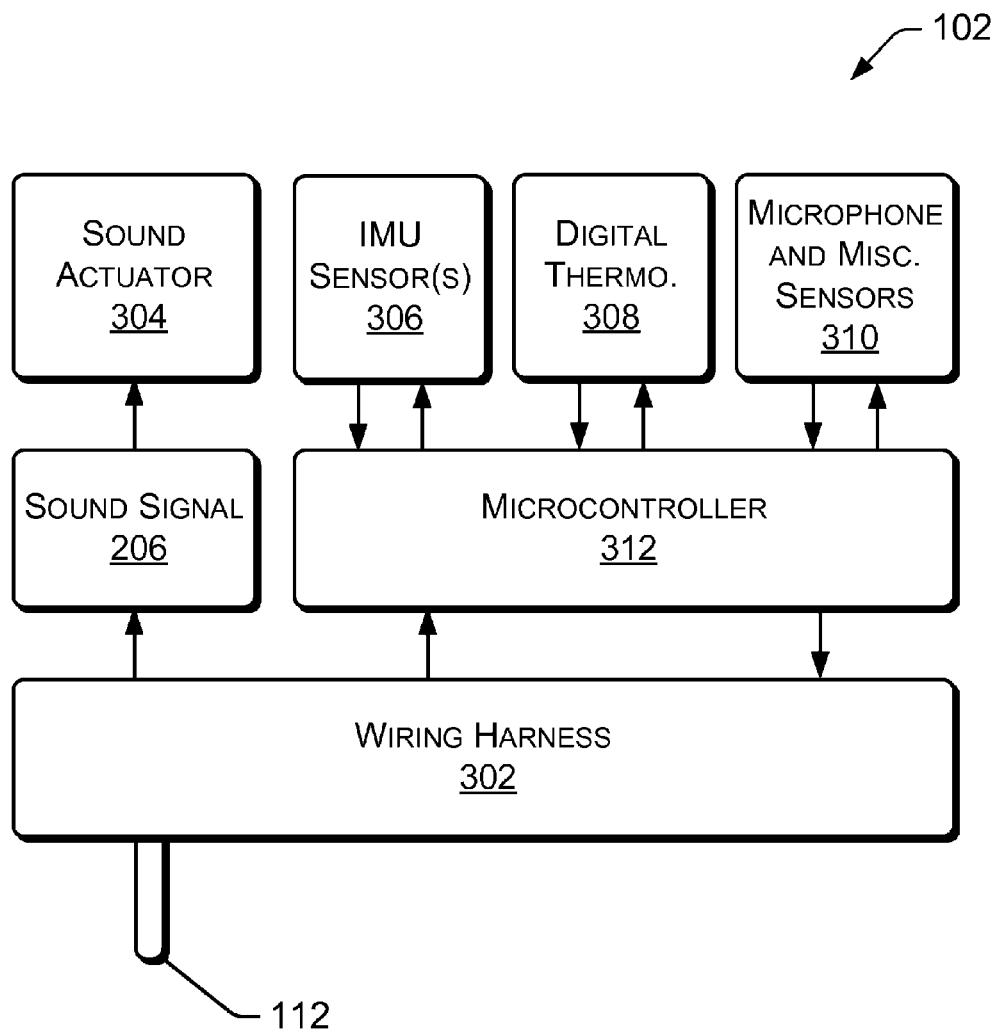
FIG. 3 is a diagram showing an example arrangement of components in an I/O device of an earphone-based game controller and health monitor.

FIG. 3 is a diagram showing an example arrangement of components in an I/O device 102 (seen in FIG. 1). The I/O devices 102, 104 may be similarly constructed. However, to save costs, it may be beneficial to locate certain sensors in only on one of the two I/O devices. An inertial measurement unit—e.g., an accelerometer—may be included in both I/O devices 102, 104. Use of separate accelerometers, one in each I/O device, allows a user to input "complex" accelerometer data by moving the I/O devices independently. Thus, different movements of the two accelerometers allow more complex input data to be provided to application(s) operable on the mobile device than is possible with only one accelerometer. In the example of FIG. 3, the I/O device 102 is shown in a block format showing representative functionality. The functionality may be instantiated by use of components that may include: a microprocessor; memory device(s); application specific integrated circuits and/or other logic devices; and one or more input or output devices and/or sensors. These components and/or their functionality may be combined and/or separated into one or more devices, as indicated by construction technologies and design requirements.

A wiring harness 302 may provide electrical connectivity between the I/O devices 102, 104 and the base 110 (if present) or to the mobile device 106 (e.g., if the functionality of the base is included in the mobile device). The wiring harness 302 may include the wiring 108 seen in FIG. 1, together with any required connections, fasteners, strain relief devices, etc. If quick connect and disconnect are desired, a jack 112 may be located at a terminal end of the wiring 108, and an associated socket may be provided in the base 110 or mobile device 106. Accordingly, the jack allows the I/O devices 102, 104 to be collectively "plugged in" to the socket of the base 110. In an alternative example, the jack 112 may be plugged into the earphone socket defined in the mobile device 106.

A sound actuator 304 may be a speaker, and may be of a type or construction found in "ear bud" earphones or larger headset earphones. In one example, a sound actuator 304 will be provide in both I/O devices 102, 104. The sound actuator 304 may receive a sound signal 206, which both provides energy and information to the sound actuator 302. The sound signal 206 may be a mono version of a stereo input, a single channel of a stereo input, or may be a single channel audio input.

The I/O device 102 may have an inertial measurement unit (IMU) 306, such as an accelerometer. The accelerometer detects movement of the I/O device 102. In some implementations, the movement will result from movement of the I/O device in a hand of the user, who may be providing input to an application, such as a video game operating on the mobile device 106. In other implementations, the movement will result from movement of the user's head, while wearing the I/O devices 102, 104 as "ear buds." The IMU sensors 306 may receive power as an input and provide accelerometer data as an output.

A digital thermometer 308 may be provided in one or both I/O devices. Since the I/O device 102 may be worn by a user as an ear bud style earphone, the digital thermometer 308 may provide data indicating a body temperature of the user. The body temperature may be used as input for health-related application(s) operable on the mobile device 106.

A microphone and/or other miscellaneous sensors 310 may also be provided in one or both I/O devices. A microphone may provide health-related information about the user, such as heart rate, respiration rate and/or respiration problems (e.g., coughing and/or wheezing) or similar. A health-related application running on the mobile device may turn off the sound actuator 304 while the microphone operates. Other sensors may be installed on one or more of the I/O devices, including a camera, a photodiode, a gyroscope, a magnetometer and/or other sensor devices(s).

A microcontroller 312 may be used to receive and process output from the IMU sensors 306 (e.g., accelerometer), digital thermometer 308, microphone 310 and other sensors. The microcontroller 312 may be and/or include a microprocessor, one or more memory device(s), an application specific integrated circuit (ASIC), a collection of cooperating processing devices, or the like. The microcontroller 312 may be configured to process the output from the sensors, such as by interpreting digital and analog signal(s), formatting data, multiplexing data, forming data packets according to a protocol, and sending data packets, etc. The microcontroller 312 and/or associated or adjacent circuitry may provide power to the sensors 306, 308, 310, if required or indicated.

Example Software Design

Figure 4:
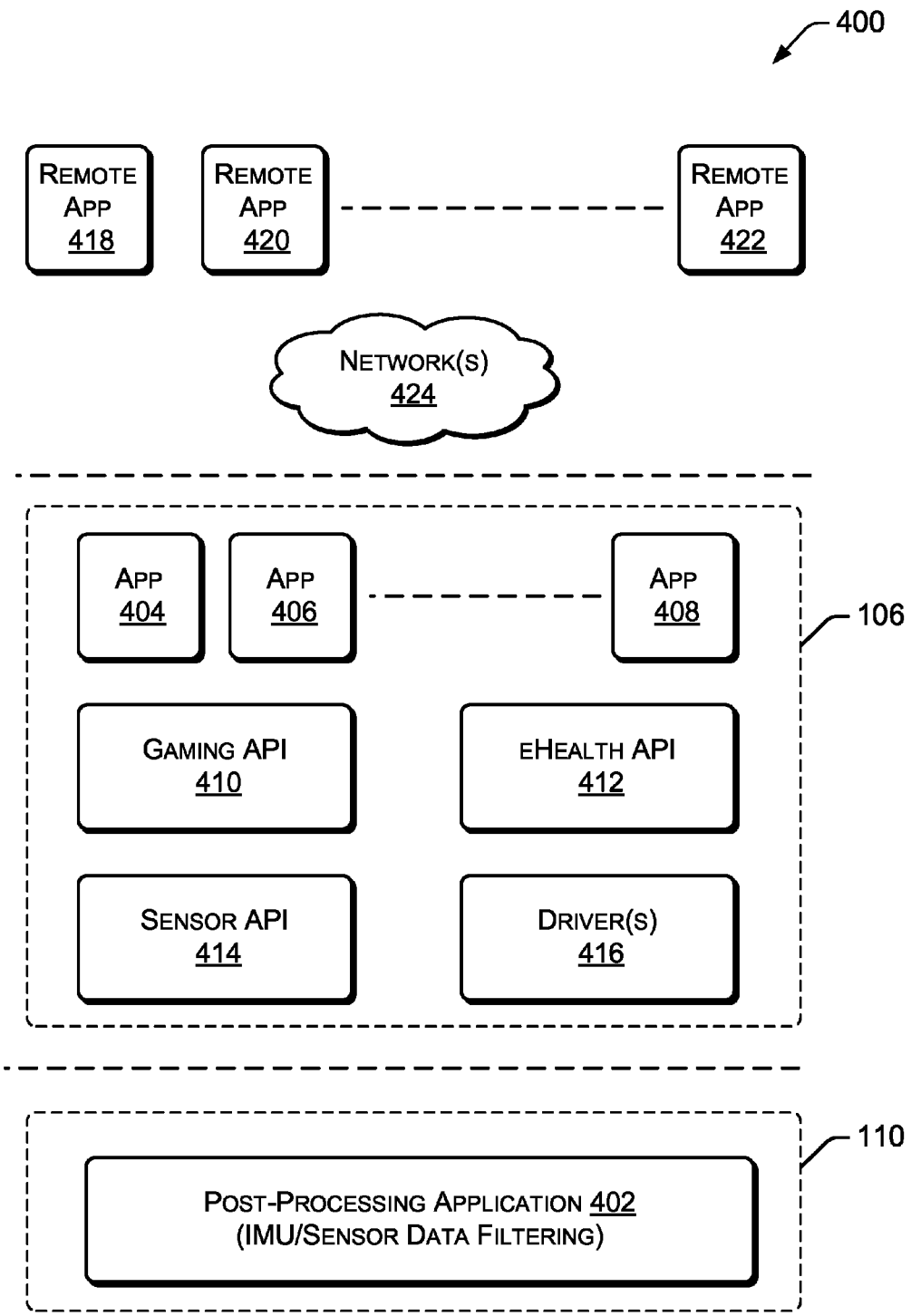
FIG. 4 is a diagram showing an example functional arrangement of an earphone-based game controller and health monitor, which may represent dedicated circuitry, software blocks, subroutines and/or programs, etc.

FIG. 4 is a diagram showing blocks representing example functionality 400 of an earphone-based game controller and health monitor. The functional blocks may be implemented by software and/or hardware structures or devices. In one example, one or more functional blocks may be implemented by aspects including a microprocessor, a microcontroller, one or more memory devices, application specific integrated circuits, software blocks, subroutines, programs, and the like.

A post-processing application 402 may be configured for operation in the base 110, or alternatively in the mobile device 106. In one example, the post-processing application 402 may include software configured to operate on the microcontroller 312 of the base 110. The post-processing application 402 may be configured to process the output from the sensors, such as by interpreting digital and analog signal(s), formatting data, multiplexing data, and forming and sending data packets, etc.

A plurality of applications 404, 406, 408 are representative of applications configured for operation on the mobile device 106. The applications may include, or be related to: video games; entertainment; business and productivity; health maintenance and health monitoring; and others. One or more applications programming interfaces (APIs) may be available for access by the applications. In the example functionality 400, a gaming API 410, an eHealth API 412 and a sensor API 414 are illustrated. Alternatively, the illustrated APIs could be combined into a unified API, or further subdivided, augmented or otherwise altered as indicated by particular circumstances and design goals. The APIs may be configured to provide the applications 404-408 with access to sensor data, control over sensors, etc. In one example, the APIs may communicate with the post-processing application 402 as a source of sensor information and control. Additionally, one or more drivers 416 may be available to configure, program, operate, control and/or interface with one or more the sensors within the I/O device(s).

In an addition or alternative to the applications 404, 406, 408, remote applications 418, 420, 422 may be available, and may be operated and/or executed by the mobile device 106 through a network 424, such as the Internet. The remote applications may be configured to access the APIs 410, 412, 414 and/or drivers 416, and to obtain sensor data from one or more I/O devices 102, 104, such as through operation of the post-processing application 402.

The applications 404-408 and 418-422 may be configured for a wide variety of purposes. By way of example, and without limiting the purposes and/or functionality of usable applications generally, a number of application topics can be indicated. Applications may use accelerometers in one or both I/O devices (ear buds) for game, video game, and health assessment and monitoring functionality. The data obtained from two accelerometers may be considered to be "complex," in that two signals may be used. If the user holds one I/O device in each hand, the accelerometer signals may be interpreted either as a single two-handed gesture or two one-handed gestures. For example, a two-handed gesture might be interpreted as the user's two hands on two spots on a (possibly imaginary) steering wheel in a video game race car. Alternatively, a video game could interpret two one-handed gestures, such as pointing a gun with one hand (e.g., left-to-right movement with the left hand) and reloading the gun with the other hand (e.g., a circular movement with the right hand).

One or more of the applications 404-408 and 418-422 may be configured to use a microphone in a manner similar to a stethoscope, such as to listen to heart rate, respiration rate, breathing issues such as coughing and wheezing, detecting chewing patterns. Additionally, applications could use input from one or more microphones to detect buzzers, smoke alarms, the approach of cars, or a fall by a user wearing the I/O devices as a headset. Additionally, applications can listen to a user's heart rate for indications that the user is exercising, and may use that information to coordinate appropriate selections of music to be played over the speakers of the I/O devices. Such an application could also provide a musical transition after a workout, such as to more mellow music. The applications may also analyze sleep, such as by use of the microphone(s) and accelerometers to check breathing rate, snoring, teeth clenching and/or grinding, and/or the signs of sleep apnea.

One or more of the applications 404-408 and 418-422 may also relate to, be involved with, and/or monitor, promote or enhance exercise and fitness. Exercise patterns, trips and falls, estimated calories burned, minutes spent walking, running, standing and sitting may all be estimated, recognized and/or determined. A thermometer may measure body temperature, and may correlate temperature data with exercise and/or health data. A camera may be used by one or more application, for such purposes as distinguishing weather, lighting levels, inside and outside locations, and for reasons of user safety and/or public safety.

Example Methods

The example methods of FIGS. 5-14 can be understood in part by reference to the configurations of FIGS. 1-4. However, FIGS. 5-14 contain general applicability, and are not limited by other drawing figures and/or prior discussion. Each method described herein is illustrated as a collection of acts, blocks or operations in a logical flow graph, which represent a sequence of operations that can be implemented in hardware (e.g., application specific integrated circuits), software (e.g., execution of statements on a processor attached to memory), or a combination thereof. The methods may include storing, in a memory communicatively coupled to a processor, computer-executable instructions for performing a method, such as a method to implement an earphone-based game controller and health monitor, and executing the instructions on the processor.

In the context of software, the operations represent computer-executable instructions stored on one or more computer-readable storage media that, when executed by one or more processors, perform the recited operations. Such storage media, processors and computer-readable instructions can be located within the system (e.g., the system and example functionality 400 of FIG. 4) according to a desired design or implementation. The storage media associated with the data processor 214 and/or microcontroller 312 and seen in FIGS. 2 and 3 are representative of storage media generally, both removable and non-removable, and of any technology. Thus, the recited operations represent actions, such as those described in FIGS. 5-14, and may be performed under control of one or more processors configured with executable instructions to perform actions indicated. Generally, computer-executable instructions include routines, programs, objects, components, data structures, and the like that perform particular functions or implement particular abstract data types. The order in which the operations are described is not intended to be construed as a limitation, and the described operations may be combined in different orders and/or in parallel to implement the method. The above discussion may apply to other methods described herein.

Additionally, for purposes herein, a computer-readable media may include all or part of an application specific integrated circuit (ASIC) or other hardware device. Such a hardware device may be configured to include other functionality, including functions performed in game controlling and/or health assessing and/or monitoring. Accordingly, within such an integrated circuit, one or more processors are configured with executable instructions, which may be defined by logic, transistors or other components, or on-board memory.

In contrast, communication media may embody computer-readable instructions, data structures, program modules, or other data in a modulated data signal, such as a carrier wave, or other transmission mechanism. As defined herein, computer-readable media does not include communication media.

Example Accelerometer Data Handling

Figure 5:
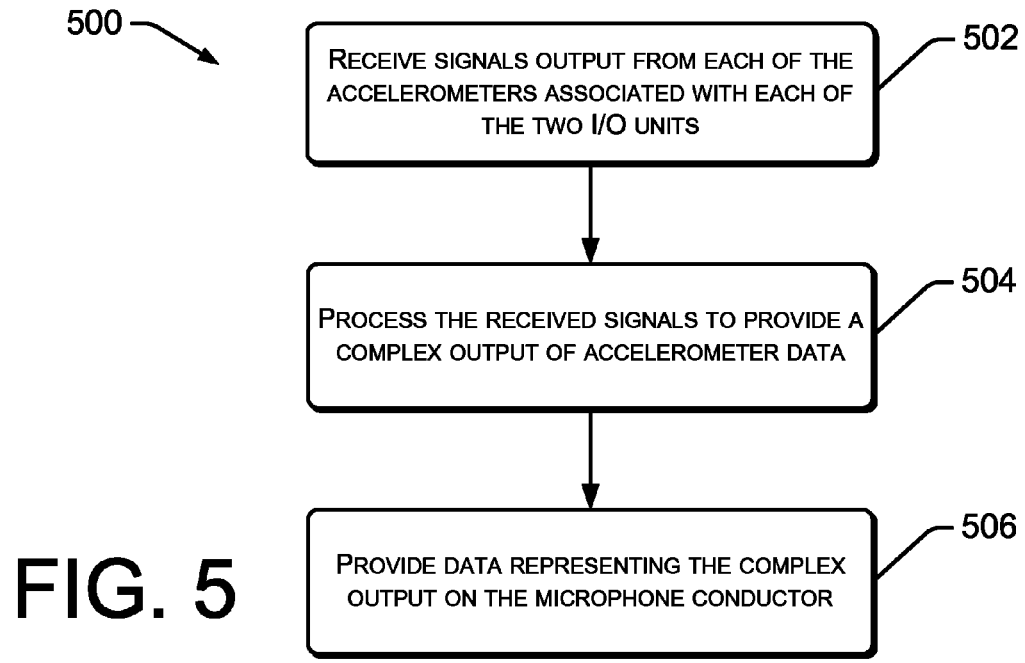
FIG. 5 is a flow diagram illustrating an example process by which accelerometer data is received from two or more accelerometers and is configured as "complex" output.
Figure 6:
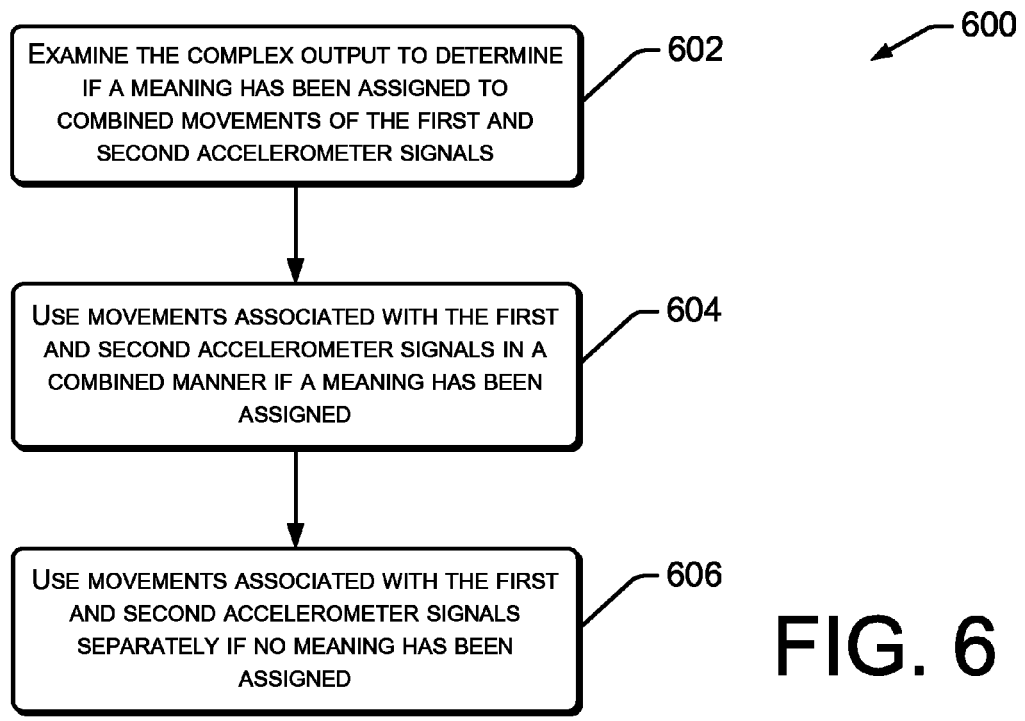
FIG. 6 is a flow diagram illustrating an example process by which complex accelerometer data may be examined and utilized.
Figure 7:
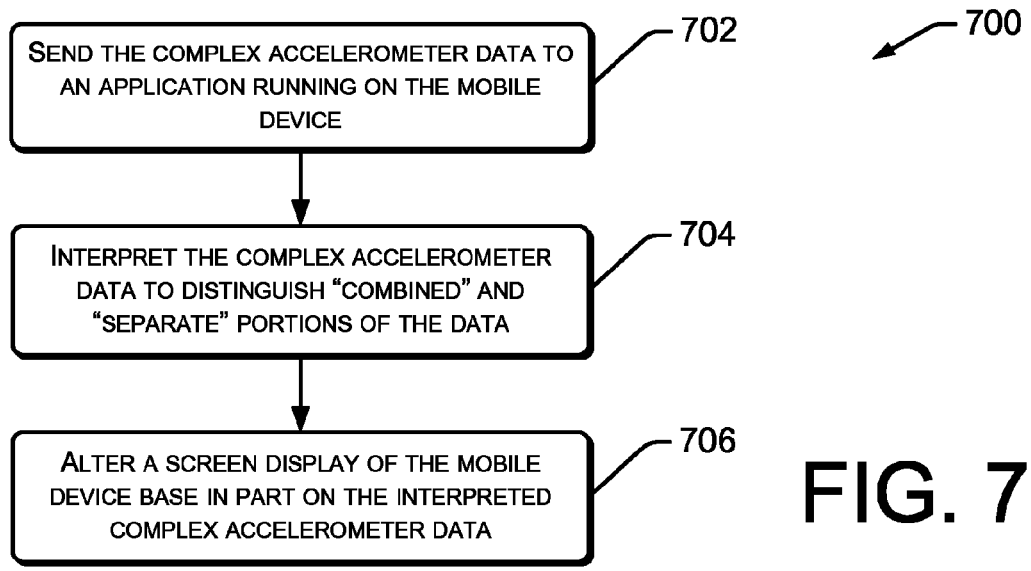
FIG. 7 is a flow diagram illustrating an example process by which accelerometer data may be used to alter a screen display, such as a screen display of a mobile device.

Accelerometer data may be used for applications related to gaming, entertainment, education, health maintenance and diagnosis, and other topics. In example embodiments using two I/O devices, each I/O device may be configured with an accelerometer, and data from the two accelerometers may be used in a separate or combined manner. FIGS. 5-7 illustrate examples of accelerometer data handling.

FIG. 5 is a flow diagram illustrating an example process 500 by which accelerometer data is received from one or more accelerometers. In one example, the accelerometer data may be derived from the operation of two accelerometers, and may be configured as "complex" output, in that two accelerometer signals may be provided. The two signals may result from user action such as holding one I/O device in each hand. Such complex accelerometer output signals may be interpreted by an application as either as a single two-handed gesture or two one-handed gestures. Applications, such as video games, may utilize the accelerometer data, possibly in addition to other data, as user input to the game.

At operation 502, signals output from accelerometers in each of two I/O devices are received. In the context of the example of FIG. 1, signals from two I/O devices 102, 104 may be received at the base unit 110 and/or at the mobile device 106. As seen in FIG. 3, each I/O device may include an accelerometer, configured as an inertial measurement unit 306.

At operation 504, the received accelerometer signals are processed to provide output, which may be complex. Referring to the context of the example of FIG. 2, the accelerometer signals may be received by the microcontroller 314 within the I/O device and/or by the data processor 214 of the base unit 110.

At operation 506, accelerometer data representing a complex movement may be put on the microphone conductor for transmission to a base unit, if present, and then for use by application(s) running on a mobile device. In the context of the example of FIG. 2, the complex accelerometer data is placed by the data processor 214 on the microphone input for transmission to the mobile device 106 (see FIG. 1). In the context of the example of FIG. 1, the microphone input of the mobile device is a port through which data may be introduced into the mobile device. Accordingly, by providing data representing the complex output of the accelerometers on the microphone conductor, the data is introduced to the mobile device and is available for applications accessible to the device, running locally and/or remotely.

FIG. 6 is a flow diagram illustrating an example process 600 by which complex accelerometer data may be examined and utilized. The data may be utilized by game (e.g., video game) applications and/or health maintenance or diagnostic applications running on, or accessible to, the mobile unit.

At operation 602, the complex output of the accelerometers is examined to determine if a meaning has been assigned to combined movements of the first and second accelerometer signals. For example, the accelerometer data may be examined to determine if it represents one two-handed gesture or two one-handed gestures.

At operation 604, if a meaning has been assigned to the combined accelerometer data obtained from two accelerometers, then the data is used in a combined manner by an application or other consumer of the data. For example, if a single two-handed gesture has been assigned to, or has been associated with, the accelerometer data and/or gesture, then the data is used in the combined manner.

At operation 606, if no meaning has been assigned to the combined accelerometer data, then the data from each accelerometer is used individually by the consumer of the data (e.g., an application). For example, if no single two-handed gesture has been assigned, then the accelerometer data may be used as two one-handed gestures.

FIG. 7 is a flow diagram illustrating an example process 700 by which complex accelerometer data may be examined, segmented and utilized. The complex output of the accelerometers is examined to distinguish: (1) portions of the complex accelerometer data wherein a combined meaning is applied to data from the two accelerometers, from (2) portions of complex accelerometer data wherein a separate meaning is applied to accelerometer data from each of the two accelerometers. Examples of data having combined meaning include data associated with two-handed gestures. In contrast, examples of data having separate meaning include data associated with one or more one-handed gestures. Once identified and/or distinguished, the different portions of data may be appropriated analyzed, interpreted and/or utilized.

At operation 702, complex accelerometer data is sent by the I/O devices to the mobile device 106 or to the base 110, for processing. Depending on the configuration of the earphone-based game controller and health monitor 100, a base unit 110 may interface between the I/O devices 102, 104 and the mobile device 106. In such a configuration, the complex accelerometer data may be sent by the I/O devices to an application (e.g., post-processing application 402) operating on the data processor 214 of the base unit 110. In other configurations, the accelerometer data may pass through the base unit 110 (if present) and be received by an application running on the mobile device 106 or operating remotely, such as in a data or Internet-based cloud.

At operation 704, the complex accelerometer data is interpreted to distinguish "combined" and "separate" portions of the data. That is, portions of the complex accelerometer data that involve combined input of the two accelerometers are distinguished from portions of the data that involved separate interpretation of movements of the two accelerometers. In one example, the motions of the two accelerometers are considered, and if they are consistent with motions that have previously been assigned a combined meaning, then the combined motions are distinguished from separate motions of the two accelerometers.

At operation 706, a screen display of a mobile device may be altered based at least in part on the interpreted complex accelerometer data. In one example, a video game application operating on the mobile device may react to accelerometer input by changing content displayed on the screen. The accelerometer input may change screen content based on either a combined meaning of two accelerometers or according to separate meanings of the two accelerometers.

Example Health Monitor

Figure 8:
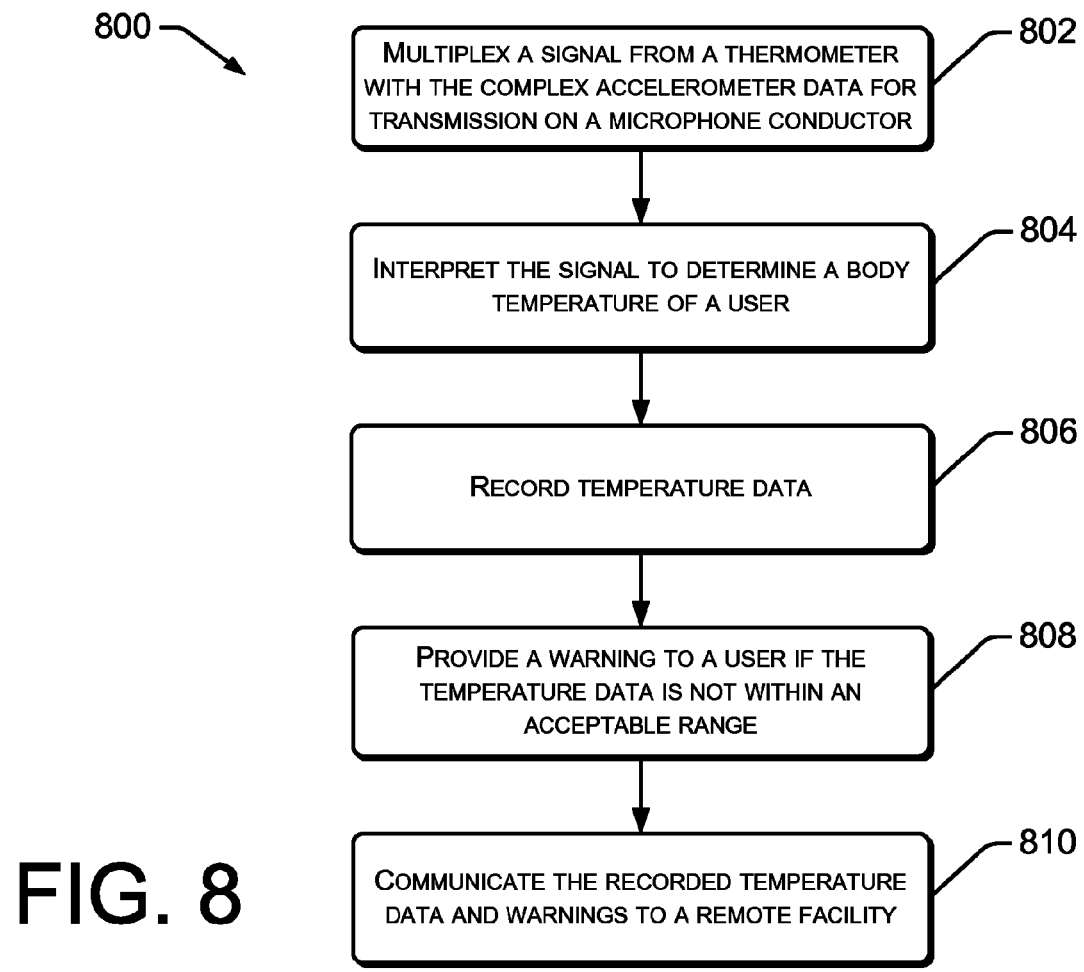
FIG. 8 is a flow diagram illustrating an example process by which temperature data, such as body temperature of a user, may be processed.

FIG. 8 is a flow diagram illustrating an example process 800 by which temperature data, such as body temperature of a user, may be processed. In the context of example FIG. 3, a digital thermometer 308 is present on one or both of the I/O devices 102, 104. A raw data signal from the digital thermometer may be combined with data from the IMU (accelerometer) and other sensors, such as a thermometer or microphone. The combination may be performed by the post-processing application 402 operating on the microcontroller 312. Data from the digital thermometer may be input to an application running on the mobile device 106, which may provide health status and diagnostics to the user.

At operation 802, a signal from a thermometer may be multiplexed with the complex accelerometer data for transmission on a microphone conductor. In the context of the example of FIG. 3, the digital thermometer 308 provides raw data to the microcontroller 312, which multiplexes the provided data with data from the IMU accelerometers 306 and/or other sensors, if present. The multiplexed data may be put onto a microphone conductor that is input to the mobile unit.

At operation 804, the signal from the thermometer may be interpreted by an application running on the mobile device. The interpretation may include converting an analog signal to digital, converting digital data into a representation of temperature, assigning units of measurement (e.g., Fahrenheit or Celsius), assigning a time of measurement, and/or other processing.

At operation 806, data obtained from the signal and/or the interpretation of the signal is stored. The storing may include representing the signal from the thermometer in an appropriate data structure.

At operation 808, a warning is provided to the user if the temperature data is not within an acceptable (e.g., a healthy) range. At operation 810, the recorded temperature data and/or any warnings may be communicated with a remote facility, such as a family member, doctor's office, clinic, hospital or emergency call center, etc.

Figure 9:
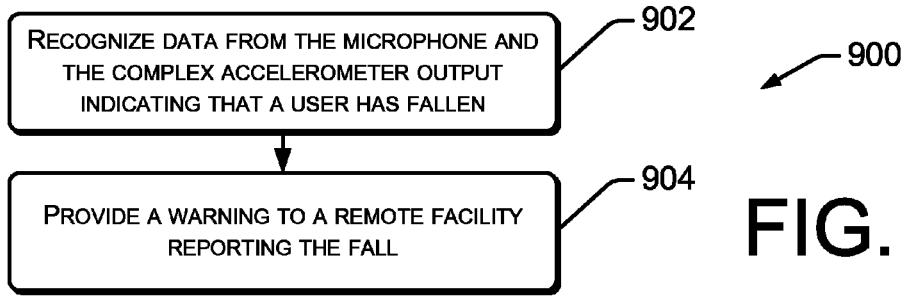
FIG. 9 is a flow diagram illustrating an example process by which accelerometer data may be processed to determine if a user has fallen.

FIG. 9 is a flow diagram illustrating an example process 900 by which accelerometer data may be processed to determine if a user has fallen. When an elderly user falls, there is particular concern that the fall may constitute a medical emergency. Elderly people are frequently unable to get up, after falling, which makes falling a particular dangerous event. Therefore, detection of a fall can be particularly important. At operation 902, data from the microphone(s) and/or accelerometer(s) is analyzed, and a data pattern indicating a user fall is recognized. At operation 904, a warning is provided to a remote facility reporting the fall. In one example, the remote facility may be a family member, doctor's office, clinic, hospital or emergency call center, such as 911.

Figure 10:
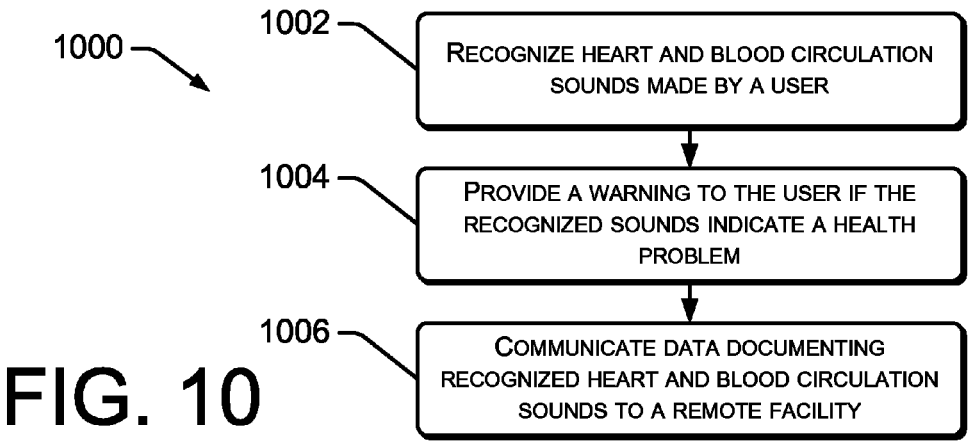
FIG. 10 is a flow diagram illustrating an example process by which data from a microphone gathers heart rate and circulation information about a user.

FIG. 10 is a flow diagram illustrating an example process 1000 by which data from a microphone may gather heart rate and circulation information about a user. At operation 1002, heart and blood circulation sounds made by a user are recognized. Such sounds may include heart beat strength, heart beat rate, heart valve noise, and noises which may indicate a heart attack (e.g., heart information combined with vocal noise). At operation 1004, a warning may be provided to a user if the recognized sounds indicate a health problem. In the context of the example of FIGS. 1 and 3, the warning may be an audio warning through the speakers 304. At operation 1006, data documenting recognized sounds is communicated to a remote facility such as a family member, doctor's office, clinic, hospital or emergency call center, such as 911.

Figure 11:
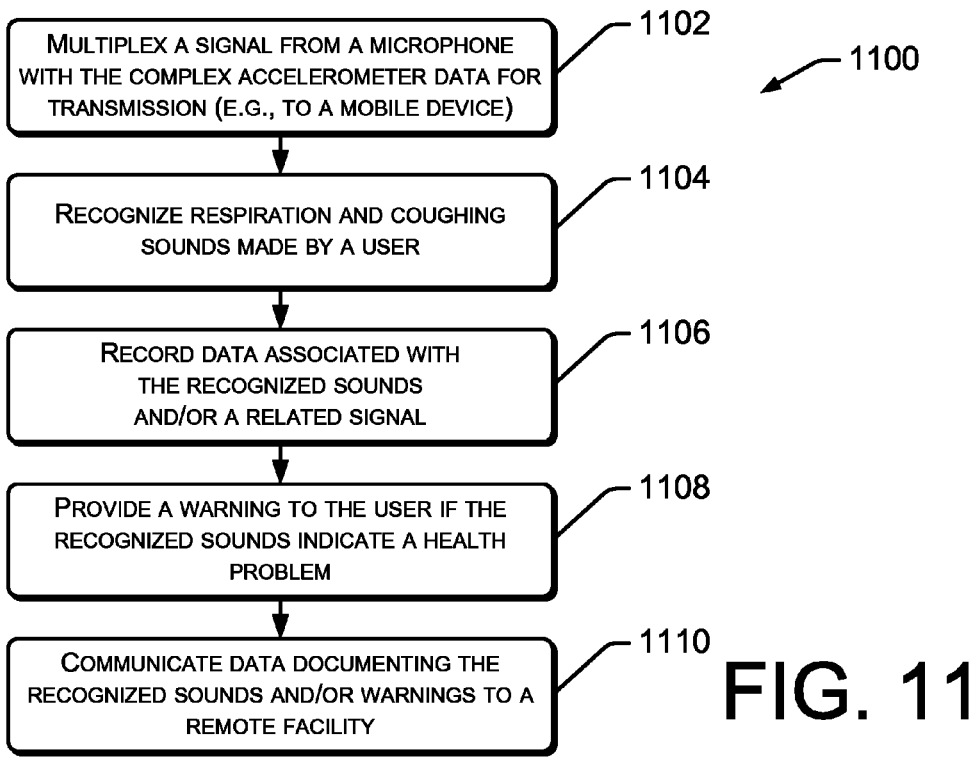
FIG. 11 is a flow diagram illustrating an example process by which data from a microphone gathers respiration information (e.g., respiration rate, coughing, etc.) about a user.

FIG. 11 is a flow diagram illustrating an example process 1100 by which data from a microphone may gather respiration information (e.g., respiration rate, coughing, etc.) about a user. Such information may be of particular importance to patients with allergies, lung disease, and other conditions. At operation 1102, a signal from a microphone may be multiplexed with accelerometer data for transmission, such as from the I/O devices 102, 104 to the base 110 or mobile device 106. In the context of the example of FIGS. 2 and 3, the microphone signal and/or microphone data may be multiplexed with accelerometer data onto the microphone input 216 by operation of the microcontroller 312. At operation 1104, respiration and coughing and related sounds are recognized. In the context of FIG. 4, the recognition may be made by the post-processing application 402 or an application 404-408, 418-422 operating on the mobile device 106. At operation 1106, data associated with the recognized sounds and/or related sounds are recorded. In the context of the example of FIG. 4, the recording may be made by an application 404-408, 418-422 operating on the mobile device. At operation 1108, a warning may be provided to the user if the recognized sounds indicate a health problem. At operation 1110, the data and/or warnings may be communicated to a remote facility, such as a family member, doctor's office, clinic, hospital or emergency call center, such as 911.

Figure 12:
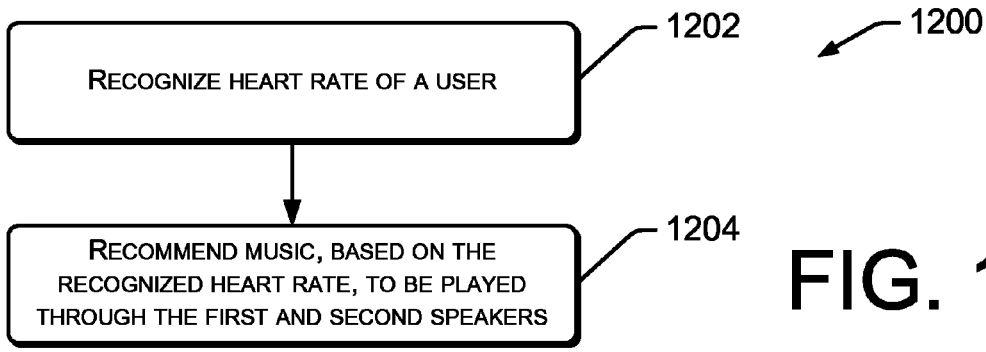
FIG. 12 is a flow diagram illustrating an example process by which music may be recommended based on heart rate of a user, which may indicate an activity level of the user.

FIG. 12 is a flow diagram illustrating an example process 1200 by which music may be recommended to a user based on heart rate of the user, which may be used as an indicator of an activity level of the user. At operation 1202, a heart rate of a user is measured. In the context of the examples of FIGS. 3 and 4, the microphone 310 may be used to gather data, which may be interpreted by the post-processing application 402 of the base 110 or a health-related application, such as an application from among applications 404-408, 418-422. The sound of any music playing at the time of heart rate measurement may be cancelled by appropriate technology, or the music may be briefly terminated. At operation 1204, music is recommended to the user, by operation of one or more application 404-408, 418-422. The recommendation may be based at least in part on the measured heart rate. In the context of the examples of FIGS. 1 and 3, the music may be played for the user through first and second speakers 304 within the I/O devices 102, 104.

Figure 13:
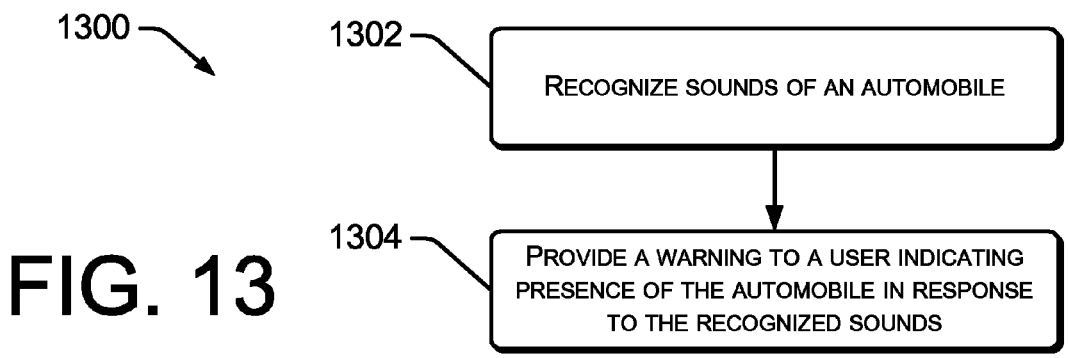
FIG. 13 is a flow diagram illustrating an example process by which information from a microphone may be used to recognize an automobile and warn a user listening to music and/or exercising.

FIG. 13 is a flow diagram illustrating an example process 1300 by which information from a microphone may be used to recognize an automobile, and warn a user of the automobile, such as when the user is listening to music and/or exercising. At operation 1302, sounds of an automobile are recognized. In the context of the examples of FIGS. 3 and 4, the sounds of the automobile may be recognized by operation of microphone 310 and by operation of an application 404 on the mobile device 106. At operation 1304, a warning is provided to a user indicating that the automobile is near. In the context of the example of FIGS. 1 and 3, the warning can include a recorded emergency declaration played to the user over the sound actuator 304.

Figure 14:
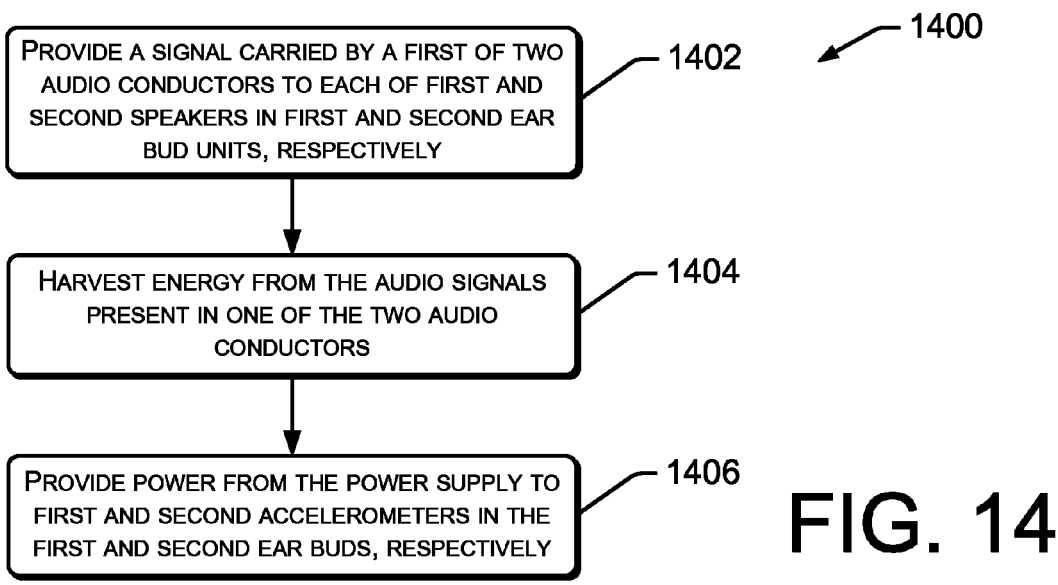
FIG. 14 is a flow diagram illustrating an example process by which an audio signal may be converted into a power supply.

FIG. 14 is a flow diagram illustrating an example process 1400 by which an audio signal may be converted into a power supply. At operation 1402, a signal carried by a first of two audio conductors is provided to each of first and second speakers in first and second ear bud units, respectively. In the context of the example of FIG. 2, left and right stereo inputs 212 corresponding to left and right tracks of an audio channel are delivered to a power conversion and audio pass-though device 210. One audio channel is "passed through" to speakers in both I/O devices, thereby providing a mono signal to each speaker. At operation 1404, energy is harvested from a second of the two stereo inputs, and thereby provides an energy source and/or a power supply. In the context of the example of FIG. 2, energy from the stereo input or conductor that is not "passed through" to speakers in one or both I/O devices is harvested. The harvested energy provides an energy source and/or a power supply for use by other components in the base unit, I/O unit(s) and/or other component or system. The frequency and amplitude of the signal may be used to regulate the voltage, amperage and/or power of the power supply. At operation 1406, the power supply may be provided to any components in the I/O devices and/or base that requires power, such as the accelerometers, digital thermometer, processors, microcontrollers, etc.

Conclusion

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A system, comprising:
an audio jack, having two audio conductors and a microphone conductor, adapted for connection to a mobile device;
a power converter to input a signal on a first of the two audio conductors and to provide a power output;
two I/O devices, each I/O device comprising:
 a speaker to output sound based on input from a second of the two audio conductors; and
 an accelerometer, powered by the power output and configured to output a signal;
a processing unit, powered by the power output, and configured for:
 receiving signals output from each of the accelerometers associated with each of the two I/O devices;
 processing the received signals to provide a complex output of accelerometer data; and providing data representing the complex output on the microphone conductor.

2. The system of claim 1, additionally comprising:
a thermometer, on at least one of the two I/O devices, to output a signal to the processing unit, the signal based on a temperature sensed by the thermometer;
wherein the processing unit combines the received signals output from the accelerometers with the signal based on the temperature sensed by the thermometer for transmission on the microphone conductor of the audio jack.

3. The system of claim 1, additionally comprising:
an application, configured for operation on the mobile device;
wherein portions of the complex output of accelerometer data are interpreted by the application to have a meaning associated with combined movement of the two accelerometers.

4. The system of claim 1, additionally comprising:
an application, configured for operation on the mobile device;
wherein portions of the complex output of accelerometer data are interpreted by the application to have a meaning associated with independent movement of the two accelerometers.

5. An ear bud system, comprising:
a power converter to input a signal on a first audio conductor and to provide a power output;
first and second I/O devices, comprising:
  first and second speakers, respectively, responsive to a second audio conductor; and
  first and second accelerometers, respectively, powered by the power output and configured to output first and second accelerometer signals, respectively;
a thermometer, in at least one of the two I/O devices, to output a thermometer signal, the thermometer signal based on a temperature sensed by the thermometer; and
a processing unit, configured for:
  combining the first and second accelerometer signals into a complex accelerometer output, portions of which may be evaluated in a first manner, considering combined movement of the first and second accelerometers, and portions of which may be evaluated in a second manner, considering separate movement of the first and second accelerometers; and
  multiplexing the complex accelerometer output and the thermometer signal as output on a microphone conductor.

6. The ear bud system of claim 5, additionally comprising:
an application, configured for operation on a mobile device; and
a sensor application programming interface (API), configured for operation on the mobile device and configured for communication with the application;
wherein the application is configured to access the thermometer signal and the complex accelerometer output by operation of the sensor API.

7. The ear bud system of claim 5, additionally comprising:
a sensor application programming interface (API), configured for operation on the mobile device;
an application, configured for operation on the mobile device and to communicate with the first and second accelerometers and the thermometer by operation of the sensor API, wherein the application is configured to:
  examine the complex accelerometer output;
  distinguish portions of the complex accelerometer output to be evaluated in the first manner from portions to be evaluated in the second manner; and
  utilize the distinguished portions as input to video game elements displayed on the mobile device.

8. The ear bud system of claim 5, additionally comprising:
a sensor application programming interface (API), configured for operation on the mobile device;
an application, configured for operation on the mobile device and to communicate with the first and second accelerometers and the thermometer by operation of the sensor API, wherein the application is configured to:
  recording temperature data;
  providing a warning to a user if the temperature data is not within an acceptable range; and
  communicating the recorded temperature data and warnings to a remote facility.

9. The ear bud system of claim 5, additionally comprising:
a sensor application programming interface (API), configured for operation on the mobile device as an interface to an audio jack port of the mobile device;
an application, configured for operation on the mobile device and to communicate with the two I/O devices by operation of the sensor API, wherein the application is configured to:
  examine the complex output to determine if a meaning has been assigned to combined movements of the first and second accelerometer signals;
  use movements associated with the first and second accelerometer signals in a combined manner if a meaning has been assigned; and
  use movements associated with the first and second accelerometer signals separately if no meaning has been assigned.

10. The ear bud system of claim 5, additionally comprising:
a microphone, in at least one of the two I/O devices, to output sound data, the sound data based on a sound sensed by the microphone; and
an application, configured for operation on a mobile device and to receive the sound data from the microphone and the complex accelerometer output, wherein the application is configured to:
  recognize data from the microphone and the complex accelerometer output indicating that a user has fallen; and
  provide a warning to a remote facility reporting the fall.

11. The ear bud system of claim 5, additionally comprising:
a microphone, in at least one of the two I/O devices, to output sound data, the sound signal based on a sound sensed by the microphone; and
an application, configured for operation on a mobile device and to receive the sound data from the microphone, wherein the application is configured to:
  recognize respiration and coughing sounds made by a user;
  provide a warning to the user if the recognized sounds indicate a health problem; and
  communicate data documenting the recognized sounds to a remote facility.

12. The ear bud system of claim 5, additionally comprising:
a microphone, in at least one of the two I/O devices, to output sound data, the sound data based on a sound sensed by the microphone; and
an application, configured for operation on a mobile device and to receive the sound data, wherein the application is configured to:
  recognize sounds of an automobile; and
  provide a warning to a user indicating presence of the automobile in response to the recognized sounds.

13. The ear bud system of claim 5, additionally comprising:
a microphone, in at least one of the two I/O devices, to output sound data, the sound data based on a sound sensed by the microphone; and
an application, configured for operation on a mobile device and to receive the sound data, wherein the application is configured to:
recognize heart and blood circulation sounds made by a user;
provide a warning to the user if the recognized sounds indicate a health problem; and
communicate data documenting recognized heart and blood circulation sounds to a remote facility.

14. The ear bud system of claim 5, additionally comprising:
a microphone, in at least one of the two I/O devices, to output sound data, the sound data based on a sound sensed by the microphone; and
an application, configured for operation on a mobile device and to receive the sound data from the microphone, wherein the application is configured to:
measure a heart rate of a user;
recommend music, based on the measured heart rate, to be played through the first and second speakers.

15. The ear bud system of claim 5, additionally comprising:
an application, configured for operation on a mobile device, and configured to adjust a frequency or amplitude of the signal sent on the first audio converter to thereby control the power output from the power converter.

16. The ear bud system of claim 5, wherein the first and second I/O devices are configured for insertion into an ear of a user, and wherein the first and second I/O devices additionally comprise:
a microphone, located inside at least one I/O device;
a gyroscope, located inside at least one I/O device; and
a magnetometer, located inside at least one I/O device;
wherein the processing unit multiplexes data from the microphone, the gyroscope and the magnetometer onto the microphone conductor.

17. A method of data input to a mobile device, comprising:
providing a signal carried by a first of two audio conductors to each of first and second speakers in first and second ear bud units, respectively;
converting a second of the two audio conductors into a power supply;
providing power from the power supply to first and second accelerometers in the first and second ear buds, respectively;
processing signals received from the first and second accelerometers to create complex accelerometer data;
sending the complex accelerometer data to an application running on the mobile device;
interpreting the complex accelerometer data to distinguish portions of the complex accelerometer data wherein a separate meaning is applied to data from each of the two accelerometers from portions of complex accelerometer data wherein a combined meaning is applied to accelerometer data from the two accelerometers; and
altering a screen display of the mobile device based in part on the interpreted complex accelerometer data.

18. The method of claim 17, wherein:
the application running on the mobile device is a video game; and
altering the screen display of the mobile device base includes using separate meanings of the two accelerometers to perform separate functions, respectively, each function controlling a separate element defined on the screen display.

19. The method of claim 17, additionally comprising:
multiplexing a signal from a thermometer with the complex accelerometer data for transmission on a microphone conductor that is in communication with the mobile device;
interpreting the signal to determine a body temperature of a user;
recording interpreted data; and
transmitting a warning if the interpreted data is out of a healthy range.

20. The method of claim 17, additionally comprising:
multiplexing a signal from a microphone with the complex accelerometer data for transmission on a microphone conductor that is in communication with the mobile device;
interpreting the signal to determine breathing rate, cough rate and respiration sounds;
recording data associated with the interpreted signal; and
transmitting a warning if the recorded data is out of a healthy range.

* * * * *